United States Patent [19]

Felix et al.

[11] Patent Number: 5,496,299
[45] Date of Patent: Mar. 5, 1996

[54] SUCTION RESERVOIR

[75] Inventors: Augustus Felix, Providence; Gary V. Halick, East Greenwich, both of R.I.

[73] Assignee: C. R. Bard, Inc., Murray Hill, N.J.

[21] Appl. No.: 310,267

[22] Filed: Sep. 21, 1994

[51] Int. Cl.6 .................................................. A61M 1/00
[52] U.S. Cl. ............................................ 604/319; 604/317
[58] Field of Search ...................... 604/73, 4–6, 317–319

[56] References Cited

U.S. PATENT DOCUMENTS

| | | |
|---|---|---|
| 3,376,868 | 4/1968 | Mondiadis . |
| 3,572,340 | 3/1971 | Lloyd et al. . |
| 3,742,952 | 7/1973 | Magers et al. . |
| 3,752,158 | 8/1973 | Kariher . |
| 3,774,611 | 11/1973 | Tussey et al. . |
| 3,779,243 | 12/1973 | Tussey et al. . |
| 3,809,086 | 5/1974 | Schachet et al. . |
| 3,871,377 | 3/1975 | Treace . |
| 3,875,941 | 4/1975 | Adair . |
| 3,900,029 | 9/1975 | Melnick et al. . |
| 4,141,361 | 2/1979 | Snyder . |
| 4,429,693 | 2/1984 | Blake et al. . |
| 4,453,937 | 6/1984 | Kurtz et al. ............................. 604/319 |
| 4,529,402 | 7/1985 | Weilbacher et al. . |
| 4,578,060 | 3/1986 | Huck et al. . |
| 4,664,652 | 5/1987 | Weilbacher . |
| 4,957,487 | 9/1990 | Gerow . |
| 4,981,474 | 1/1991 | Bopp et al. . |
| 5,112,323 | 5/1992 | Winkler et al. ......................... 604/319 |
| 5,141,504 | 8/1992 | Herweck et al. ....................... 604/317 |
| 5,275,585 | 1/1994 | Olson . |

Primary Examiner—Randall L. Green
Assistant Examiner—Mark O. Polutta
Attorney, Agent, or Firm—Kane, Dalsimer, Sullivan, Kurucz, Levy, Eisele and Richard

[57] ABSTRACT

A detachable suction reservoir provides suction to a drainage and autotransfusion system coupled with a closed wound drain to facilitate drainage of blood from the wound into a substantially rigid collection container. This blood is adapted to be transferred into a blood bag which in turn may be coupled with an administration set for reinfusion. While blood is reinfusing, blood collection into the container continues. Following autotransfusion, the suction reservoir can be converted to a suction device for blood collection directly from the closed wound drain.

6 Claims, 4 Drawing Sheets

SUCTION RESERVOIR

BACKGROUND OF THE INVENTION

With the current concern over contaminated blood and the spread of contagious disease through blood transfusions, it is becoming increasingly popular, if not desirable, to reinfuse a patient's blood drained and collected from a wound drainage site following surgery. While several systems and techniques have been proposed, there exists a need for a wound drainage collection and reinfusion system that need not rely on wall suction, is more versatile and easier to use by nurses or patient attending personnel and one that is relatively less costly to manufacture and assemble with its own portable suction generator.

SUMMARY OF THE INVENTION

A principal object of the present invention is to provide an improved closed wound orthopaedic drainage and autotransfusion system with its own portable suction generator for the simultaneous collection and reinfusion of autologous shed blood following orthopaedic surgery.

Another object is to provide an improved suction reservoir for incorporation into a system of the foregoing type and which may also be detached from the system and function as a wound drainage evacuator.

The drainage and autotransfusion system of the present invention will typically be connected by the surgeon to a closed wound drain. If desired by the surgeon, an appropriate anticoagulant may be added to the system through a conveniently located sterile port. A detachable evacuator or suction reservoir provides self-contained suction to the system to facilitate drainage from the wound. After blood has been collected in a substantially rigid collection container, it is transferred into an attached blood bag for reinfusion. Reinfusion of the blood is performed by utilizing normal blood transfusion procedures by also coupling with a standard blood administration set and utilizing the conventional gravity drip fluid flow technique. While the blood is reinfusing, blood collection can simultaneously continue into the collection container. Following autotransfusion and if prescribed, the suction reservoir can be converted to a closed wound suction device for continued blood collection.

DETAILED DESCRIPTION

Figure 1:
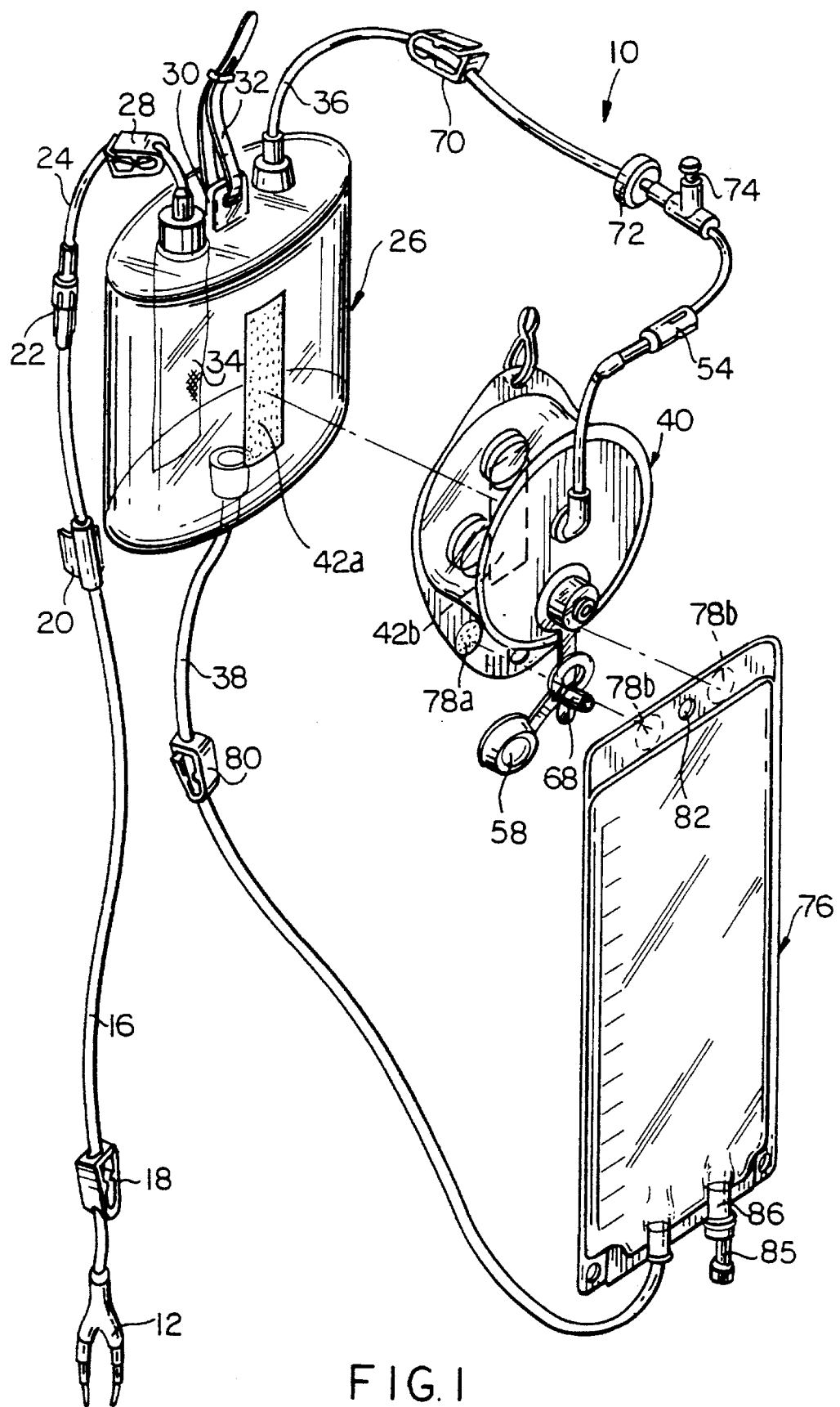
FIG. 1 is a perspective view of the closed wound orthopaedic drainage and autotransfusion system of the present invention.
Figure 2:
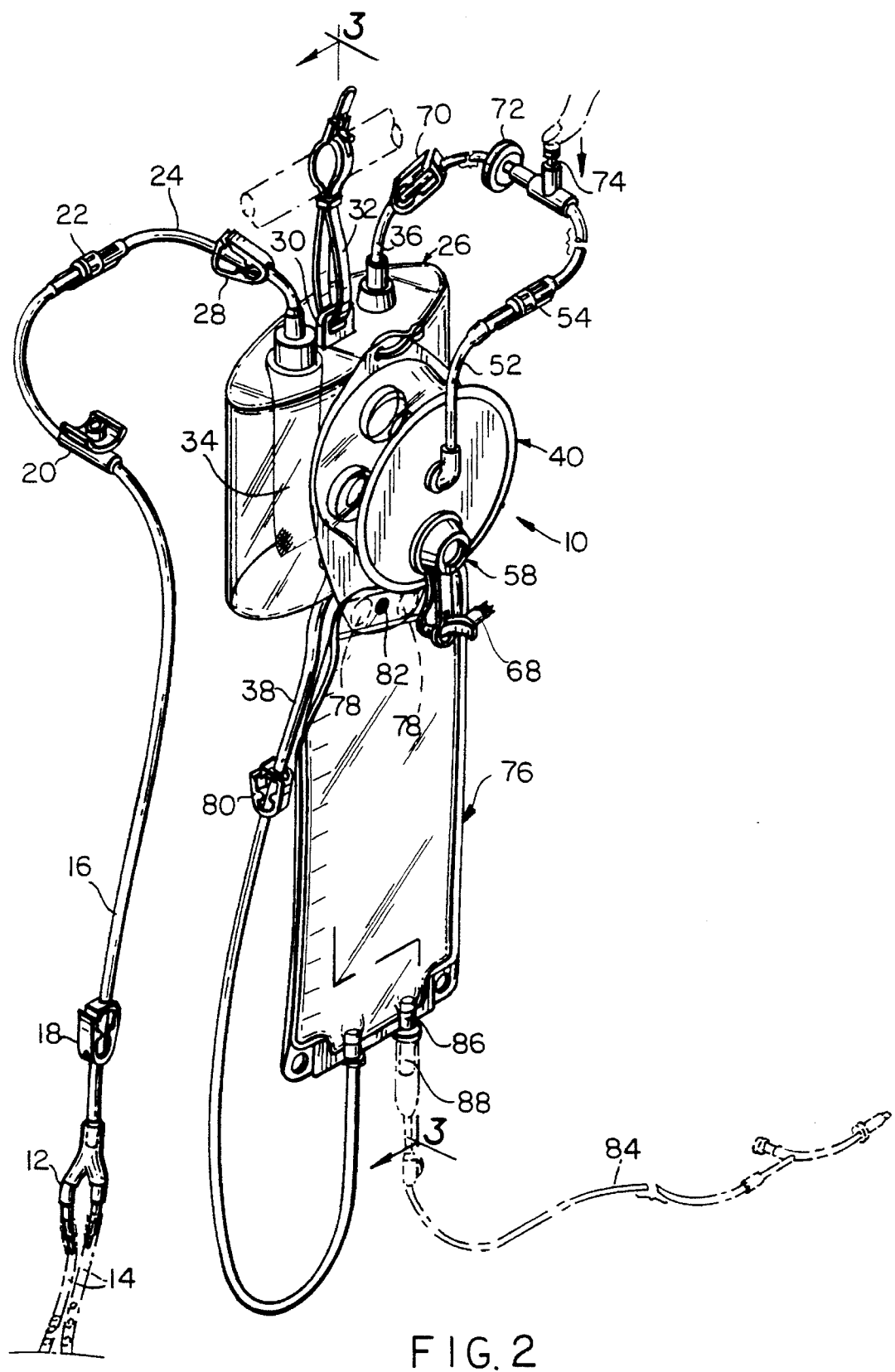
FIG. 2 is an exploded perspective view of the system of FIG. 1.
Figure 3:
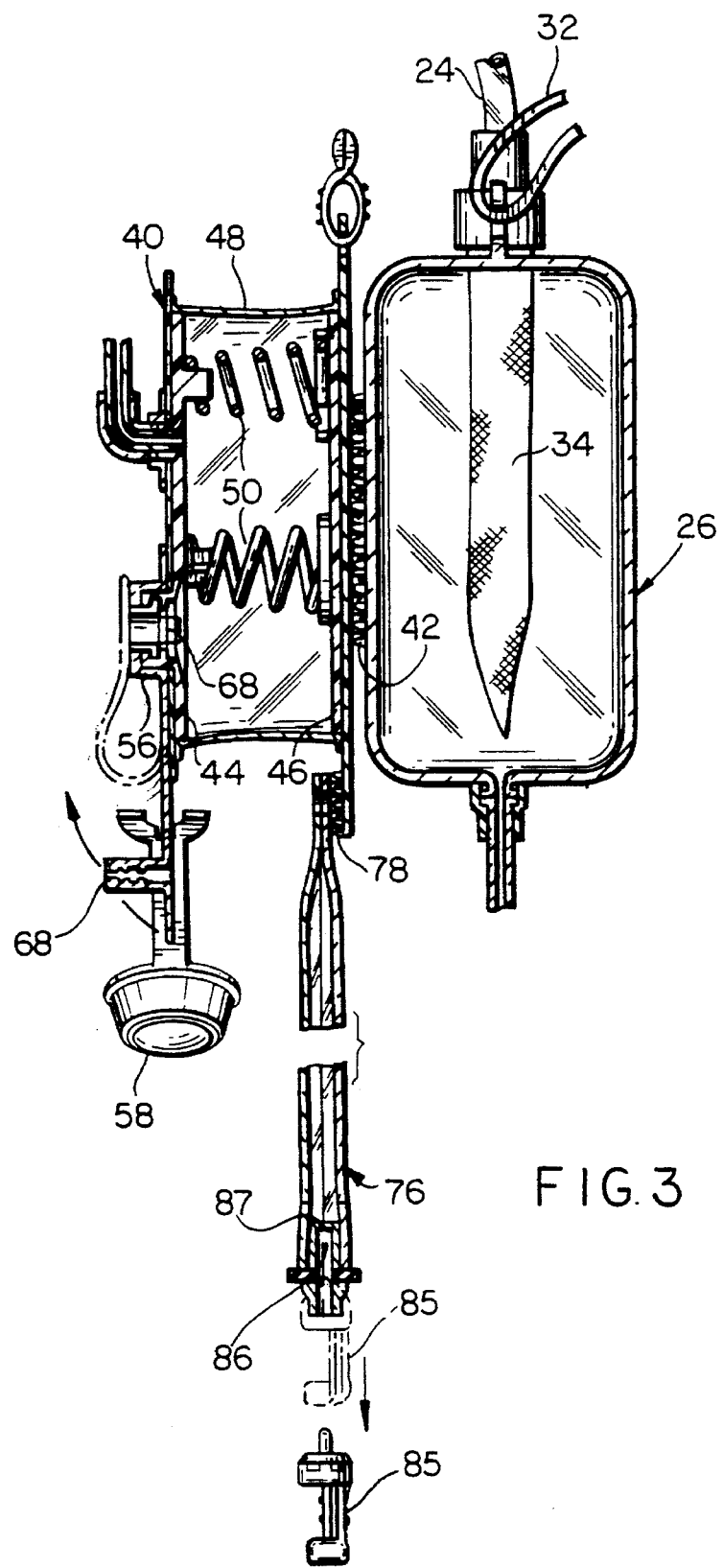
FIG. 3 is a longitudinal sectional view taken along the line 3—3 of FIG. 1.
Figure 4:
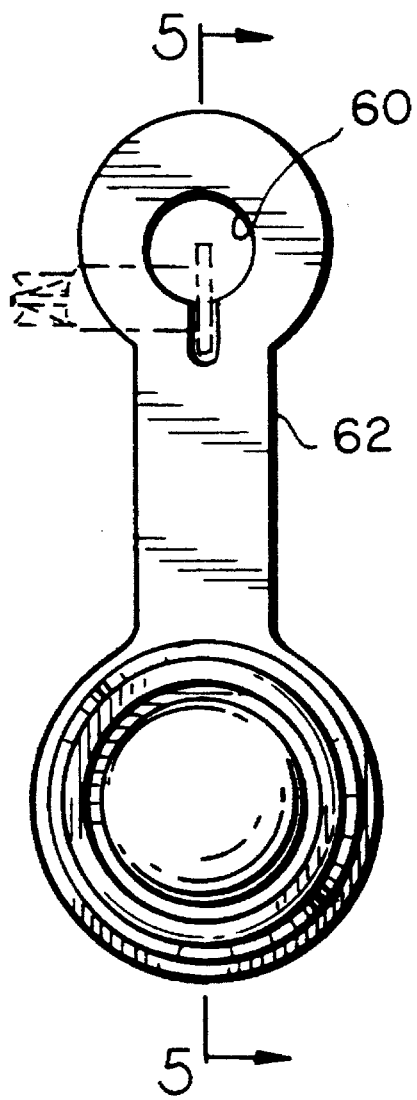
FIG. 4 is a top plan view of the tethered one way valve of the suction reservoir.
Figure 5:
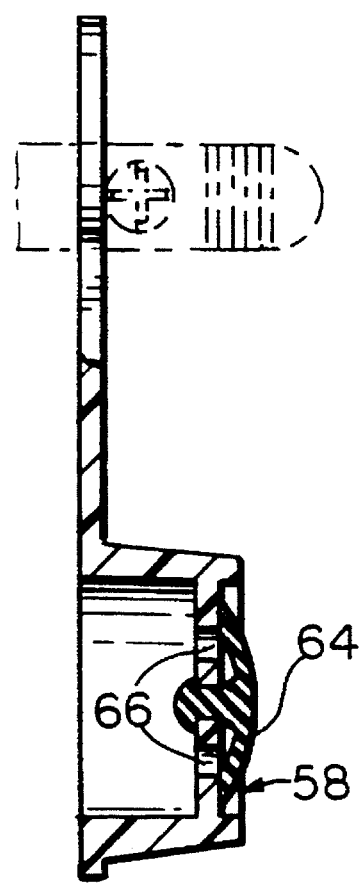
FIG. 5 is a sectional view of the valve taken along the line 5—5 of FIG. 4.

The closed wound orthopaedic drainage and autotransfusion system 10 of this invention includes a universal Y-connector 12 for connection to the closed wound drain 14. Extending from the Y-connector 12 is a suitable length of patient drainage tube 16 having a pinch clamp 18 for controlling or stopping liquid flow and a sterile self sealing injection port 20 through which an ACD-A anticoagulant or any other prescribed anticoagulant may be added to the system if desired by the surgeon. A luer lock type of connector 22 may be included to connect tube 16 to tube 24 anchored or fixed to and in fluid communication with the interior of transparent rigid container 26. Pinch clamp 28 is associated with tube 24 to control or stop liquid flow.

The transparent rigid container 26 includes an upwardly extending apertured lug 30 that receives strap 32 for suspending or hanging the assembly 10 from a bed rail or IV pole. An internal pre-filter 34 is mounted on and extends interiorly of the container 26 and filters the autologous shed blood flowing into the container from tube 24. In accordance with a successful embodiment of assembly 10, the filter 34 may possess 260 micron porosity. Suction is supplied to the interior of container 26 through fixed tube 36 and the liquid collected in the container is adapted to be transferred through fixed transfer tube 38 as will be explained in detail shortly.

Suction is supplied to the interior of the container 26 by an evacuator or suction reservoir 40 which is adapted to be releasably connected to the side of container 26 by a Velcro® brand hook and loop fastener 42 or any other suitable fastener. The suction reservoir 40 includes a pair of spaced circular plates 44 and 46 connected by a resilient sleeve 48 and adapted to be urged in their spaced apart relationship by internal springs 50. A fixed inlet tube 52 is adapted to be coupled with tube 36 by a luer lock connector 54. A valve controlled outlet 56 is adapted to purge the suction reservoir 40 of air upon collapsing the resilient sleeve 48 by manually squeezing the plates 44 and 46 together. A one-way outlet umbrella valve 58 is adapted to be detached from the outlet 56 and coupled thereto by means of opening 60 on strap or tether 62 to permit disposal of exudate collected in the reservoir 40 into a bag when and if the reservoir is connected directly to the wound. The umbrella valve 58 includes a flexible disc 64 covering openings 66 for sealing the reservoir interior from the ambient. When the reservoir 40 is collapsed the flexible disc 64 flexes outwardly to permit air within the reservoir to vent through the openings 66. When the valve 58 is disassociated from the outlet 56, the latter may be sealed off by attached plug 68 to seal the interior of the reservoir 46 from the ambient.

The tube 36 has a pinch clamp 70 associated therewith and an interposed filter 72 which according to a successful embodiment may be a 1.2 micron hydrophobic bacteria air filter. A transfer button 74 serving as a vent valve is also interposed in tube 36 and when depressed releases suction in the system or in the suction reservoir 40 and consequently the container 26.

The inlet of a blood transfusion bag 76 is connected to the container 26 by the tube 38 and may be suspended from the reservoir 40 by a Velcro® brand hook and loop fastener 78 or any other suitable fastener. The tube 38 may also possess a pinch clamp 80. The top of the bag 76 is provided with a hole 82 to facilitate suspending the bag from an IV pole during reinfusion. In this regard, a standard blood administration set 84 may be coupled with the bag 76 by initially removing the protective cover or plug 85 of the spike port 86 having a puncturable membrane 87 closing the bag outlet by means of an interposed standard blood transfusion filter 88 with a membrane puncturing trocar or needle and which typically is a 20–40 micron microaggregate blood filter. The administration set 84 will typically include a drip chamber and flow control clamp as well as the usual needle and trocar or adaptor to its ends.

In using the closed wound orthopaedic drainage and autotransfusion system 10, it is initially removed from its protective pouch (not shown) using sterile techniques. The pinch clamp 80 located on tube 38 between collection container 26 and the blood reinfusion bag 76 is closed to prevent fluid from entering the bag prior to blood transfer. Using an aseptic technique, the universal Y-connector 12 located at the end of the patient drainage tube 16 is connected to the appropriate size wound drain 14. If anticoagulant is to be used, it can be injected into the system 10 prior to blood collection through the injection port 20. In practice, 25–35 ml of ACD-A can be added for every 250 ml of blood collected. This is consistent with the 1:7 to 1:10 anticoagulant/blood ratio. In this regard, pinch clamp 18 or the patient drainage tube 16 between the injection port 20 and patient is closed. The desired amount of ACD-A anticoagulant is aspirated into a syringe, and then injected through the injection port 20 which should be elevated above the container 26. The pinch clamp 18 is opened to begin collection of autologous shed blood. The container 26 should be periodically agitated during collection to help insure the proper mixture of anticoagulant and blood. If gravity collection is desired, the suction reservoir 40 is not compressed. If suction drainage is desired, the tethered one-way umbrella valve 58 is coupled with the outlet port 56. The plates 44 and 46 of the reservoir 40 are compressed which will create a negative pressure in the container 26. It may be necessary to repeat this step periodically as the collection continues.

During transportation it will prove beneficial not to wet filter 72, otherwise drainage will automatically be shut off. In order to prevent this occurring, the pinch clamp 70 is closed and the system 10 is placed on the bed during transportation. Loss of blood into the suction reservoir 40 is thus prevented by closing pinch clamp 70. Should the filter 72 become wet either through overfilling, malpositioning or not closing the pinch clamp 70, prior to placing the container 26 on its side, drainage will automatically be shut off as stated. In order to resume drainage, the container 26 is placed in an upright position and the transfer button 74 is pressed or depressed to release or vent the negative pressure in the suction reservoir 40. Clearing of the tube 36 from the container 26 to the filter 72 may be facilitated by tapping the housing of the filter 72 with the transfer button 74 depressed. After the filter is cleared of fluid, the system 10 may be recharged by compressing the plates 44 and 46 of suction reservoir 40.

When the container 26 is full or it is desired to reinfuse the collected blood, the transfer tube 38 is uncoiled, if previously coiled, and the blood bag 76 is positioned below the collection container 26. The pinch clamp 18 on the patient drainage tube 16 is closed and the pinch clamp 80 on the transfer tube 38 is opened. The transfer button 74 is depressed and held in this position until all the blood has drained from the container 26 into the blood bag 76. The pinch clamp 80 on the transfer tube 38 is then closed and the pinch clamp 18 on the patient tube is opened followed by compression of the plates 44 and 46 of the reservoir 40 to continue collection under suction.

The initial quantity of blood collected may be reinfused by initially removing the protective cover of the spike port 86 from the blood bag 76. A standard blood filter 88 is inserted into the spike port 86. A standard blood administration set 84 is coupled with the filter 88 if not already combined. The bag 76 is then suspended from an IV pole. The blood filter 88 and fluid administration set 84 are primed in usual fashion and air is purged from the administration set 84. The administration set 84 may now be attached to the patient access and blood will be reinfused by gravity. Before the drip chamber of the administration set 84 empties, the clamp on the administration set 84 should be closed. In this event additional quantities of the patient's blood will be reinfused, the blood bag 76 may be left hanging on the IV pole until blood is ready to transfer from the container 26. In the event, the clamp on the blood administration set 84 should be closed and the blood bag 76 should be lowered below the container 26. The above described transfer procedure may now be performed.

When it is determined not to collect the patient's blood any longer for autotransfusion, but to continue to drain the wound, the clamps 80 and 18 on the respective blood transfer tube 38 and patient drainage tube 16 are closed. The suction reservoir 40 is removed from the container 26 and the one way valve 58 is removed from the port 56. The reservoir is disconnected from the container 26 at the luer lock connector 54, and the container 26 is disconnected from the patient tube 16 at the luer lock connector 22. The suction reservoir is then connected directly to the patient drainage tube 16 by connecting the mating luer lock connector halves. The reservoir plates 44 and 46 are compressed towards one another and the port 56 is closed by the tethered one way valve 58. The container 26 and bag 76 may then be properly discarded.

When it is desired to empty the suction reservoir 40 that is connected directly to the patient drainage tube 16, the clamp 18 is closed and the port 56 is opened by removing the tethered one way valve 58. The reservoir 40 is turned over and the plates 44 and 46 of the reservoir 40 are compressed until the contained fluid is removed. For continued drainage, the plates 44 and 46 of the reservoir 40 are compressed and the port 56 is closed by the tethered one way valve 58. The clamp 18 on the patient drainage tube 16 may now be released or opened to resume the collection process.

Thus, the several aforenoted objects and advantages are most effectively attained. Although a single somewhat preferred embodiment of the invention has been disclosed and described in detail herein, it should be understood that this invention is in no sense limited thereby, but its scope is to be determined by that of the appended claims.

What is claimed is:

1. A suction reservoir means including a pair of circular plates, a resilient sleeve connecting the plates, internal springs urging the plates in a spaced apart relationship, a valve controlled outlet through which air is adapted to be purged from the interior of the suction reservoir means upon collapsing the resilient sleeve by manually squeezing the plates towards one another, the valve controlled outlet including a one way valve means including openings and an umbrella valve including a flexible disc covering the openings for sealing the suction reservoir means interior from the ambient, upon squeezing the plates towards one another the flexible disc flexes outwardly to uncover the opening and permit air within the suction reservoir means to vent through the openings, coupling means for removably mounting the one way valve means on the valve controlled outlet.

2. The invention in accordance with claim 1 wherein the suction reservoir means has fastening means for releasably fastening the suction reservoir means to a blood collection bag.

3. A suction reservoir means including a pair of circular plates, a resilient sleeve connecting the plates, internal springs urging the plates in a spaced apart relationship, a valve controlled outlet through which air is adapted to be purged from the interior of the suction reservoir means upon collapsing the resilient sleeve by manually squeezing the plates towards one another, the valve controlled outlet including a one way valve means including openings and an umbrella valve including a flexible disc covering the openings for sealing the suction reservoir means interior from the ambient, upon squeezing the plates towards one another the flexible disc flexes outwardly to uncover the opening and permit air within the suction reservoir means to vent through the openings, the one-way valve means being removable from the valve controlled outlet and being on a tether for securing the one-way valve means to the suction reservoir means when the one-way valve means is removed from the valve controlled outlet.

4. The invention in accordance with claim 1 wherein a removable plug on a tether is adapted to close the valve controlled outlet and is adapted to remain on the suction reservoir means when the plug is removed from the valve controlled outlet.

5. The invention in accordance with claim 1 wherein the suction reservoir means has fastening means for releasably fastening the suction reservoir means to a rigid blood collection container.

6. A suction reservoir means including a pair of circular plates, a resilient sleeve connecting the plates, internal springs urging the plates in a spaced apart relationship, a valve controlled outlet through which air is adapted to be purged from the interior of the suction reservoir means upon collapsing the resilient sleeve by manually squeezing the plates towards one another, the valve controlled outlet including a one way valve means including openings and an umbrella valve including a flexible disc covering the openings for sealing the suction reservoir means interior from the ambient, upon squeezing the plates towards one another the flexible disc flexes outwardly to uncover the opening and permit air within the suction reservoir means to vent through the openings, the suction reservoir means having fastening means for releasably fastening the suction reservoir means to a blood collection bag, the one-way valve means being removable from the valve controlled outlet and being on a tether for securing the one-way valve means to the suction reservoir means when the one-way valve means is removed from the valve controlled outlet, a removable plug on a tether being adapted to close the valve controlled outlet and being adapted to remain on the suction reservoir means when the plug is removed from the valve controlled outlet, the suction reservoir means having fastening means for releasably fastening the suction reservoir means to a rigid blood collection container.

* * * * *